United States Patent [19]

Ilardi et al.

[11] Patent Number: 5,393,466
[45] Date of Patent: Feb. 28, 1995

[54] FATTY ACID ESTERS OF POLYALKOXYLATED ISETHIONIC ACID

[75] Inventors: Leonora Ilardi, Valley Cottage, N.Y.; Mark Rerek, Fanwood, N.J.; Michael Massaro, Ridgefield Park, N.J.; Christine Wenzel, Rutherford, N.J.

[73] Assignee: Lever Brothers Company, Division of Conopco, Inc., New York, N.Y.

[21] Appl. No.: 45,951

[22] Filed: Apr. 12, 1993

Related U.S. Application Data

[63] Continuation-in-part of Ser. No. 796,748, Nov. 25, 1991.

[51] Int. Cl.$^6$ ............................................. C11D 1/12
[52] U.S. Cl. ................................... 252/549; 252/557; 252/DIG. 16; 554/92; 554/90
[58] Field of Search ............................ 554/92; 252/549; 260/513, 409

[56] References Cited

U.S. PATENT DOCUMENTS

| | | | |
|---|---|---|---|
| 3,029,264 | 4/1962 | Alphen et al. | |
| 3,823,185 | 7/1974 | Schlossman | 260/513 |
| 4,954,282 | 9/1990 | Rys | 252/117 |

FOREIGN PATENT DOCUMENTS 974124  12/1961  United Kingdom .

Primary Examiner—Paul Lieberman
Assistant Examiner—Necholus Ogden
Attorney, Agent, or Firm—Ronald A. Koatz

[57] ABSTRACT

The present invention provides novel fatty acid esters of alkoxylated isethionic acid and compositions comprising these compounds.

4 Claims, No Drawings

FATTY ACID ESTERS OF POLYALKOXYLATED ISETHIONIC ACID

CROSS REFERENCES

This is a continuation-in-part of U.S. Ser. No. 07/796,748, filed Nov. 25, 1991.

BACKGROUND OF THE INVENTION

1. Field of the Invention

The present invention relates to fatty acid esters of polyalkoxylated isethionic acid as well as to compositions comprising the novel fatty acid esters.

2. Prior Art

The use of alkoxylated isethionates having the formula

H—(OCH$_2$CH$_2$)$_n$SO$_3$Na is known in the art, for example, from U.S. Pat. No. 3,823,185 to Schlossman.

The use of fatty acid esters of isethionate, e.g., sodium cocoyl isethionate having the formula

$$\text{CH}_3(\text{CH}_2)_{10-12}\overset{\overset{\text{O}}{\|}}{\text{C}}-\text{OCH}_2\text{CH}_2\text{SO}_3^-\text{Na}^+$$

is also known in the art (see for example, Rys et al., U.S. Pat. No. 4,954,282).

U.S. Pat. No. 3,029,264 to Alphen discloses fatty-acyl-oxyalkane sulphonates of formula RCOOR'SO$_3$M, wherein R' may be —CH$_2$CH$_2$OCH$_2$CH$_2$—. Fatty acid of esters polyalkoxylated compounds are neither taught nor suggested.

SUMMARY OF THE INVENTION

It has now been found that fatty acid esters of alkoxylated isethionates, particularly polyalkoxylated isethionates, are superior to fatty acid esters of identical non-alkoxylated isethionates in mildness (as suggested by in vitro zein solubilization tests and confirmed by in vivo occlusive patch tests). In addition, the alkoxylated isethionates perform as well or better than nonethoxylated equivalents (as measured by Ross-Miles foam heights and/or with lather volume tests). These compounds are also much more calcium tolerant.

Specifically, the present invention relates to ethoxylated isethionate surfactants having the general formula:

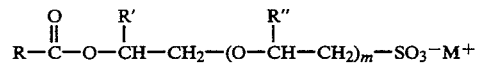
$$\overset{\overset{\text{O}}{\|}}{\text{R}-\text{C}}-\text{O}-\overset{\overset{\text{R}'}{|}}{\text{CH}}-\text{CH}_2-(\text{O}-\overset{\overset{\text{R}''}{|}}{\text{CH}}-\text{CH}_2)_m-\text{SO}_3^-\text{M}^+$$

wherein R is an alkyl group having 8 to 18 carbons, m is an integer from 2 to 4, R' and R" are hydrogen or an alkyl group having from 1–4 carbons, and M+ is a monovalent cation such as, for example, sodium, potassium or ammonium.

As indicated above, such compounds have been found to be superior to similar compounds where m equals 0 (i.e., non-ethoxylated compounds) in both mildness and performance.

As indicated in more detail below, the surfactant compound of the invention may be prepared by reacting a sulfoalkoxyalcohol and a fatty acid by direct esterification. Since sulfoalkoxyalcohol may be formed by the reaction of sodium isethionate and a mixture of alkylene oxide groups, the resulting sulfoalkoxyalcohol can contain a mixture of alkoxylated groups (e.g., the molecule might contain both ethoxy and propoxy groups). Stated differently, if m>1 (i.e., 2–4), the R" group may differ from one alkoxylate group to another.

Further, since the sulfoalkoxyalcohol obtained is then reacted with fatty acids which typically comprise a mixture of R groups, the ethoxylated isethionate produced comprise a mixture of R groups as well (ranging from C$_8$ to C$_{18}$).

In the second embodiment of the invention, the invention relates to the use of the novel surfactant compounds and compositions containing these compounds. Among the compositions in which the surfactant may be used include both heavy and light-duty liquid detergent compositions, detergent bar compositions and personal product compositions (e.g., shampoos or facial cleansers or foam baths).

For reasons noted above, the compounds used in the compositions of this aspect of the invention are mixtures of alkoxylated isethionates, wherein each alkoxylated isethionate might contain a mixture of alkoxylated groups and wherein there is a mixture of alkyl chain lengths among the various alkoxylated isethionates.

DETAILED DESCRIPTION OF THE INVENTION

The present invention provides novel alkoxylated isethionate surfactants having the formula:

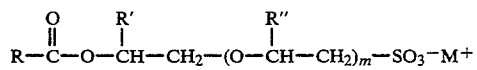
$$\overset{\overset{\text{O}}{\|}}{\text{R}-\text{C}}-\text{O}-\overset{\overset{\text{R}'}{|}}{\text{CH}}-\text{CH}_2-(\text{O}-\overset{\overset{\text{R}''}{|}}{\text{CH}}-\text{CH}_2)_m-\text{SO}_3^-\text{M}^+$$

wherein R is an alkyl group having 8 to 18 carbons, m is an integer from 2 to 4, R' and R" are hydrogen or an alkyl group having from 1–4 carbons and M+ is a monovalent cation such as, for example, active, potassium or ammonium.

When these surfactant molecules were compared to molecules identical except that they were not alkoxylated, significant improvements in both mildness and performance were observed. The compounds are also much more calcium tolerant.

PREPARATION

The alkoxylated molecules of the invention may be prepared in several ways. In one embodiment of the invention, the molecules may be prepared by first preparing an alkoxylated isethionate via the sulfonation of a corresponding chloroalkoxy lower alcohol (e.g., 2-(2-chloroethoxy)ethanol) and then treating the sulfoalkoxy lower alcohol (e.g., 2-(2-sulfoethoxy)ethanol) so formed with an alkoyl chloride wherein the alkoyl group has 8 to 18 carbons (e.g., lauroyl chloride) to form the described ester.

An example of this process is set forth below:

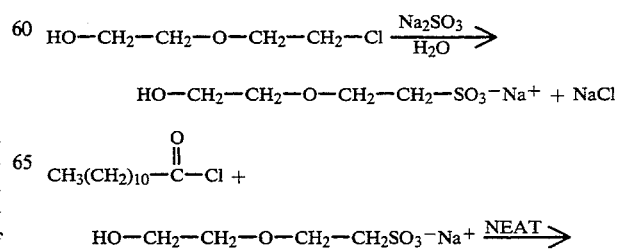
$$\text{HO}-\text{CH}_2-\text{CH}_2-\text{O}-\text{CH}_2-\text{CH}_2-\text{Cl} \xrightarrow[\text{H}_2\text{O}]{\text{Na}_2\text{SO}_3}$$

$$\text{HO}-\text{CH}_2-\text{CH}_2-\text{O}-\text{CH}_2-\text{CH}_2-\text{SO}_3^-\text{Na}^+ + \text{NaCl}$$

$$\text{CH}_3(\text{CH}_2)_{10}-\overset{\overset{\text{O}}{\|}}{\text{C}}-\text{Cl} +$$

$$\text{HO}-\text{CH}_2-\text{CH}_2-\text{O}-\text{CH}_2-\text{CH}_2\text{SO}_3^-\text{Na}^+ \xrightarrow{\text{NEAT}}$$

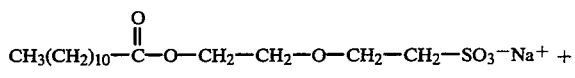

The reaction is described in greater detail in the examples below.

In another embodiment, the sulfoalkoxyalcohol may be produced by a reaction of alkylene oxide and sodium isethionate and a resulting reaction product then reacted with a fatty acid via acid catalysis to form the desired ester. An example of this direct esterification reaction is set forth below:

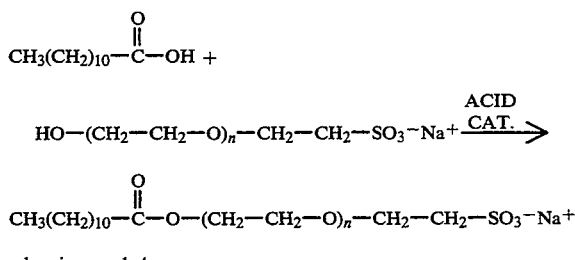

wherein n = 1-4

As indicated above, since the sulfoalkoxyalcohol can be formed from a mixture of alkylene oxides, the resulting alcohol may comprise a mixture of alkoxy groups (e.g., might contain both ethoxy and propoxy groups). As also indicated above, the fatty acid is generally a mixture of fatty adds of varying chain lengths and the reaction product will accordingly generally be a mixture of alkoxylated isethionates with a distribution of various alkyl groups.

COMPOSITIONS

The alkoxylated isethionate surfactant compounds of the invention may be used in any cleaning or cleansing composition as may be known to those skilled in the art. For example, the components may be used in various personal washing compositions such as detergent bars, hand or body cleansers, shampoos as well as other compositions where mild surfactants might be desired (e.g. light duty liquid dishwashing compositions). The surfactants might also be used in a general cleaning or cleansing compositions.

To the extent that the surfactants may be used in any cleaning or cleansing composition known to those skilled in the art, it will be understood by those skilled in the art that the surfactants may be used in combination with one or more cosurfactants in binary active compositions, ternary active compositions, etc.

These examples are not intended to be exhaustive of the compositions in which such mild surfactants might be used and other compositions in which such mildness might be desirable would be apparent to those skilled in the art.

In general the compositions comprise 2-85% of a surfactant selected from the group consisting of anionic, nonionic, cationic, ampholytic and zwitterionic surfactants or mixtures thereof and the compound or a mixture of the compounds of the invention.

Examples of the many surfactants which may be used are set forth in U.S. Pat. No. 4,318,818 to Letton et al., hereby incorporated by reference into the present specification.

The present invention is further illustrated by the following examples which are not intended to be limiting in any way.

EXAMPLE 1

Preparation of Sodium Lauroyl Monoethoxy Isethionate Preparation of Sodium 2-(2-Sulfoethoxy)ethanol Into a three-necked, 250 ml round-bottomed flask equipped with water condenser, magnetic stir bar, oil bath, and temperature-controlled hot plate stirrer was placed 150 mL distilled deionized water and 50.2 g (0.398 moles) $Na_2SO_3$. This mixture was stirred till all the inorganic salt was dissolved. To this was added 50.0 g (0.398 moles) of freshly distilled 2-(2-Chloroethoxy)ethanol. Upon addition, a two phase reaction mixture was noted due to the insolubility of the starting organic in water. The mixture was heated to reflux for 24 hours. After this time, a clear, colorless, one phase reaction mixture was noted. Approximately 80% of the water was removed under reduced pressure using a rotary evaporator leaving a thick, colorless, opaque gel. This was poured into two crystallizing dishes and dried in a vacuum oven at 45° C. for 48 hours. After this time, 524 g of a white, brittle solid was recovered from one dish. It was analyzed to contain 23.7% NaCl. The other dish contained 245 g of a white solid analyzed to contain 10.2% NaCl. The total weight of product recovered was 620 g which is a 94.3% yield. The material can be recrystallized from ethanol and water to remove the sodium chloride and purify the material. 1H NMR (200 MHz, $D_2O$, TMS): d3.2 (2H, t); d3.62-3.75 (4H,m); d3.9 (2H, t).

Preparation of Sodium Lauroyl Monoethoxy Isethionate from Sodium 2-(2-sulfoethoxy)ethanol Into a 100 mL three-necked round-bottomed flask equipped with mechanical stirrer, oil bath with temperature controlled hot plate, inlet tube connected to a nitrogen source, and an outlet tube connected to a base (NaOH soln) trap, was placed 23.49 g (0.122 moles) of the previously prepared sodium 2-(2-Sulfoethoxy)ethanol and 26.80 g (0.123 moles) of distilled lauroyl chloride. The mixture was stirred and heated to 85° C. resulting in a white, viscous homogenous liquid. IR of the reaction after 30 min. showed completed condensation by the absence of the carbonyl stretch at 1,800 $cm^{-1}$ for the acid chloride and the appearance of the product ester carbonyl at 1740 $cm^{-1}$. The reaction was placed under vacuum using a diaphragm pump to remove the HCl produced in the reaction. The resulting solid was washed with acetone, filtered and dried in a vacuum oven. A yield of 39.4 g (86%) was obtained. The material was recrystallized from 175 mL ethanol/100 mL water producing fine, needle-like crystals; 27.3 g recovered. Hyamine analysis of this material showed approximately 100.0% activity. Lauric acid analysis: 0.60%. Water: 0.8%.

1H NMR (200 MHz, TMS, $D_2O$): d0.86 (3H, broad t); d1.0-1.7 (18H, m); d2.36 (2H, t); d3.18 (2H, t); d3.73 (2H, broad t); d3.87 (2H, t); d4.23 (2H, broad t).

EXAMPLE 2

Preparation of Sodium Lauroyl Diethoxy Isethionate
Preparation of Sodium 2-r2-(2-Sulfoethoxy)ethoxy]ethanol Into a three-necked, 250 mL round-bottomed flask equipped with water condenser, magnetic stir bar, oil bath, and temperature controlled hot plate stirrer was placed 100 mL of distilled deionized water and 32.2 g (0.295 moles) $Na_2SO_3$; the mixture was stirred until all salt was dissolved. To this was added 45 g (0.266 moles) of freshly distilled 2-[2-(2-Chloroethoxy)ethoxy]ethanol and the mixture was heated to reflux. Upon addition, the starting chloroethanol appeared as a second phase floating on top of the water. After 6 hours, a clear colorless reaction mixture resulted. HPLC analysis of the reaction mixture indicated that no starting chlorethoxyethanol remained. The reaction was placed under reduced pressure to remove most of the water resulting in a clear, colorless gel. The mixture was dried thoroughly in a vacuum oven to remove all water. A standard silver nitrate titration was conducted to assay for the percentage of sodium chloride in this material. The material was used as is in the acid chloride preparation of the ethoxylated active.

1H NMR (200 MHz, D20, TMS), d3.2 (2H, t); d3.62–3.75 (8H, m); d3.9 (2H, t).

Preparation of Sodium Lauroyl diethoxy Isethionate from Sodium 2-[2-(2-sulfoethoxy)ethoxy]ethanol (Acid Chloride Preparation)

Into a 250 mL three-necked, round-bottomed flask equipped with mechanical stirrer, oil bath with temperature controlled hot plate stirrer, inlet tube connected to a nitrogen source, and an outlet tube connected to a base (NaOH soln) trap, was placed 59.14 g (0.251 moles) of the previously prepared sodium 2-[2-(2-Sulfoethoxy)ethoxy]ethanol and 57.4 g(0.262 moles) of freshly distilled lauroyl chloride. The mixture was stirred and heated to 65° C. The reaction mixture took on an opaque, white appearance. After 30 minutes, the condensation appeared complete by IR showing the disappearance of the acid chloride carbonyl and the appearance of the product carbonyl at 1740 $cm^{-1}$. The reaction mixture was placed under reduced pressure using a diaphragm pump to remove HCl that was generated in the reaction. The resulting light tan colored solid was dissolved in water and its pH was adjusted from 2 to 7 using a dilute $NaHCO_3$ solution and the water was removed by freeze drying. The solid obtained amounted to 114 g; hyamine titration of this mixture indicated an 87% yield based on the starting 2-[2-(2-Chloroethoxy)ethoxy]ethanol. The material was recrystallized three times from ethanol/water. The analysis of the final product showed about 98% activity (hyamine titration).

1H NMR (200 MNz, $D_2O$, TMS): d0.88 (3H, broad t); d1.0–1.7 (18H, m); d2.36 (2H, t); d3.20 (2H, t); d3.67–3.80 (6H, m); d3.88 (2H, t); d4.24 (2H, broad t).

EXAMPLE 3

Preparation of Sodium Lauroyl Diethoxy Isethionate via Direct Esterification Into a glass reactor consisting of a ground glass 100 mL cylindrical bottom piece and a four-neck top piece which is fitted with a thermocouple, a mechanical stirrer, a teflon nitrogen-gas inlet tube and a water condenser was placed 71.9 g (0.359 moles) of lauric acid, 0.151 g of Zinc Oxide catalyst and an approximately 50% solution of previously prepared sodium 2-[2-(2-Sulfoethoxy)ethoxy]ethanol (62.54 g (0.265 moles) in water). Nitrogen sparging at 40 cc/min was started and the reaction mixture was stirred and heated. At 45° C. the fatty acid began to melt and at 110° C., water began to boil off and was collected along with a small amount of fatty add. After the water was removed, the reaction was heated to 235° C. for 90 minutes. After this time, the heat was removed and the mixture was allowed to cool and solidify. IR analysis of the reaction mixture showed carbonyl stretches at 1740 $cm^{-1}$ and 1710 $cm^{-1}$ indicating the product and the starting acid respectively. Hyamine titration of the mixture indicated a 81% activity.

EXAMPLE 4

Various characteristics of mono or di-ethoxylated isethionates were compared to nonethoxylated isethionate and the results are set forth below:

| Active | CMC (mM) | Krafft Pt. (0° C.) | Foam Ht. mm | % Zein Solub. | $Ca^{+2}$ Needed for prec. (ppm) |
|---|---|---|---|---|---|
| Sodium Lauroyl Isethionate | 6.2 | 24 | negligible | 55 | 51 |
| Sodium Lauroyl Monoethoxy Isethionate | 4.3 | 24 | 165/159 | 42 | 2400 |
| Sodium Lauroyl Diethoxy Isethionate | 2.7 | <0 | 154/151 | 35 | >4000 |

Each of these characteristics, how they are quantified, and an explanation of the significance of these numbers is set forth in greater detail below.

1. Critical Micelie Concentration (CMC)

The CMC is defined as the concentration of a surfactant at which it begins to form micelies in solution. Specifically materials that contain both a hydrophobic group and a hydrophilic group (such as surfactants) will tend to distort the structure of the solvent (i.e., water) they are in and therefore increase the free energy of the system. They therefore concentrate at the surface, where, by orienting so that their hydrophobic groups are directed away from the solvent, the free energy of the solution is minimized. Another means of minimizing the free energy can be achieved by the aggregation of these surface-active molecules into clusters or micelies with their hydrophobic groups directed toward the interior of the cluster and their hydrophilic groups directed toward the solvent.

The value of the CMC is determined by surface tension measurements using the Wilhemy plate method. While not wishing to be bound by theory, it is believed that a low CMC is a measure of surface activity (i.e., lower CMC of one surfactant versus another indicates the surfactant with lower CMC is more surface active).

In this regard, it is believed that lower CMC signifies that lesser amounts of a surfactant are required to provide the same surfactancy benefits as a surfactant with higher CMC.

As can be seen from the table above, both mono and di-ethoxylated have lower CMC values and are therefore believed to provide more effective surfactancy.

2. Krafft Points

The temperature at and above which surfactants begin to form micelles instead of precipitates is referred to as Krafft point (Tk) and at this temperature the solubility of an ionic surfactant becomes equal to its CMC.

Kraft point was measured by preparing a 1% dispersion of the surfactant in water. If the surfactant was soluble at room temperature, the solution was cooled to 0° C. When the surfactant did not precipitate out, its Krafft point was considered to be <0° C. If it precipitated out, the solution was slowly warmed with stirring in a water bath. The temperature at which the precipitate dissolved was determined to be the Krafft point.

If the Krafft point was above room temperature, the solution was first heated rapidly to dissolve all the surfactant. It was then cooled until precipitation occurred, and was then slowly warmed to determine the Kraft point described above.

While not wishing to be bound by theory, it is believed that lower Krafft points are indicative of a surfactant being more soluble in aqueous system. In addition, it is believed that surfactants with lower Krafft points are easier to formulate in multi-electrolyte systems because of their greater tolerance to salt.

From the table above, it can be seen that the monoethoxy material has the same Krafft point as the nonethoxy material. However, the diethoxy material has a much lower Kraft point indicating greater solubility and salt tolerance as discussed above.

3. Foam Height

Foam is an important attribute in many consumer products (e.g., consumer products). Foam is one of the dominant factors that determines the commercial value of products such as shampoo, soap, etc. Also, acceptability of many consumer products is closely related to the quality and texture of the foam they produce (psychological aspect).

Since most of the foaming data on surfactants is typically obtained by the Ross-Miles method (Ross, J. and Miles, G. D., Am. Soc. For Testing Material Method D1173-53 Philadelphia, Pa. (1953); Oil & Soap (1958) 62:1260) the foaming ability of these surfactants was also acquired using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature (often 60° C.) by means of a water jacket. The height of the foam produced in the cylindrical vessel is read immediately after all the solution has run out of the pipette (initial foam height) and then again after a given amount of time (generally, 5 min).

Using this method, the foam production (measured initially) and foam stability (the height after 10 minutes) are reported. All of the foaming was achieved at 45° C. in water with 120 ppm hardness. The foam height is represented in millimeters (mm).

As indicated in the table above, foam heights for the nonethoxylated isethionate is negligible while heights for the ethoxylated isethionates are quite high.

4. Zein Test

In vitro "Mildness" Test Assessing Mildness

Many factors have been reported to have an influence on skin irritation such as removal of skin lipids, loss of naturally occurring hygroscopic materials in the stratum corneum, adsorption, protein denaturation, and epidermal lyposomal injury. Although there are many hypotheses regarding skin irritation, it is generally believed that surfactants become irritants because they penetrate the stratum corneum which is a "barrier" and then react with the inner cells of the epidermis.

Traditionally, the study of percutaneous absorption has focused on measuring the diffusion of chemicals (e.g., surfactants through stratum corneum). Diffusion through an organ as complex as skin and its associated adnexal appendages is challenging to measure, much less to model. Another challenge of cutaneous metabolism is to assess the irritating potential, toxicity, and therapeutic potential of the penetrating compounds.

In vivo, the skin metabolism and percutaneous absorption are very difficult to measure. Finding adequate detection methods and setting up proper experiments are not easy tasks. In vitro studies however are used because of the simplicity of the experimental conditions.

We have obtained information on mildness potentials of the surfactant by carrying out in vitro tests which have been demonstrated to correlate well with in vivo tests.

In Vitro Zein Solubilization Test

Gotte (E. Gotte, Proc. Int. Cong. Surface Active Subs., 4th Brussels (1964), 3, 83–90) and Schwinger (M. J. Schwinger, Kolloid-Z.Z. Poly., (1969), 233, 898) have shown that a surfactant's ability to solubilize zein, an insoluble maize protein, correlates well with surfactant irritation potential. Specifically, the lower the amount of zein protein dissolved, the milder a surfactant is. Conversely, the more zein dissolved, the more irritating the surfactant is.

In order to test irritancy potential, a 1% solution of surfactant (30 mls) was added to 1.5 g zein and stirred at room temperature for 1 hr. Residual zein was collected and dried to constant weight. Differences between starting and residual weights were used to calculate % zein dissolved.

As seen from the table above, the decrease in zein dissolved going from the nonethoxylated material to the diethoxy material indicates a decrease in irritation potential.

5. Calcium sensitivity

The calcium ion stability of ethoxylated isethionates was measured by a modified Hart method (Witkes, et al. J. Ind. Encl. Chem., 29, 1234–1239 (1937)). The surfactant solution was titrated with a calcium ion solution. The endpoint was determined by visual observation of the cloudiness of the surfactant solution.

Many surfactants like fatty soap are known to chelate with calcium ion to form calcium salts which are usually insoluble in aqueous media. This will lead to the loss of their surfactant properties. Calcium "insensitive" surfactants have unique advantageous properties for many applications such as a formulation for a liquid cleanser. In the case of the ethoxylated isethionates, it was noticed that a large amount of calcium ion was added before precipitation was seen. For the ethoxylated isethionates, the precipitation limit was not reached even at levels well over an order of magnitude higher than the precipitation limit for the nonethoxylated isethionate.

As clearly seen from the table above, ethoxylated isethionates are much less sensitive to calcium than the nonethoxylated compound.

6. Summary

In summary, the table above shows:
(1) ethoxylated isethionates have lower CMC than nonethoxylated isethionate (lower CMC being associated with superior surfactancy);
(2) at least the diethoxy isethionate has lower Krafft point (providing better surfactant solubility and improved formulation flexibility);
(3) ethoxylated isethionates provide superior foaming;
(4) ethoxylated isethionates have greater mildness potential as indicated by the decrease in irritation potential observed when conducting in vitro zein tests; and
(5) ethoxylated isethionates are more calcium insensitive (i.e., will not precipitate as easily).

EXAMPLE 5

In Vivo Mildness Evaluation

Two toilet bar compositions containing fatty acid esters of ethoxylated isethionic acid and one toilet bar composition with a nonethoxylated counterpart were prepared and the compositions are set forth below:

| Components (% by Wt.) | Composition 1 | Composition 2 | Composition 3 |
|---|---|---|---|
| Sodium cocoyl isethionate | — | 24.89 | 49.78 |
| Sodium lauroyl diethoxy isethionate | 51.37 | 25.69 | — |
| Lauric acid | 21.6 | 10.8 | — |
| Stearic acid | — | 10.08 | 20.15 |
| Coconut fatty acid | — | 1.54 | 3.01 |
| Soap (Mixture of tallow and Coconut) | 8.02 | 8.02 | 8.02 |
| Sodium stearate | 3.01 | 3.01 | 3.01 |
| Sodium alkyl benzene sulfonate | 2.01 | 2.01 | 2.01 |
| Sodium chloride | 8.34 | 4.3 | 0.35 |
| Sodium isethionate | — | 2.34 | 4.68 |
| Water | 5.01 | 5.21 | 5.21 |
| Miscellaneous | 0.64 | 2.11 | 3.78 |

Each of the two bars (containing an ethoxylated surfactant compound of the invention) and the comparative bar (with nonethoxylated compound) were tested using a patch test which was used to assess the in vivo mildness of formulations. According to the patch test, up to six formulations can be tested at the same time on each subject using occluded patches which remain on the forearm for 24 hours. Test sites are evaluated at 6 and 24 hours following the removal of the patches for erythema. A 0–4 scale was used in which 0 is no response and 4 is severe erythema.

Results of the patch tests are shown below:

| | 6 Hours | | 24 Hours | |
|---|---|---|---|---|
| Composition | Mean Score | Std. Dev. | Mean Score | Std. Dev. |
| 1 | 0.273 | 0.47 | 0.091 | 0.3 |
| 2 | 0.273 | 0.47 | 0.091 | 0.3 |
| Comparative | 0.818 | 0.07 | 0.455 | 0.52 |

Using standard statistical measurements, "significance" (in terms of mildness) in test results is defined by 95% confidence, or better (p value <0.05). More specifically, p value is defined as the probability that two numbers are different due to chance rather than that they are really different. The lower the p value, the less likely that they are equal due to chance and the more likely that they are different. Thus a p value of 0.05 indicates that there is a 5% chance the observed differences are random coincidence and a 95% chance that the difference is a real difference. In the compositions above, both formulations 1 and 2 had a value of 0.03 (i.e., significance was established).

These tests thus clearly show that both formulation 1 containing sodium lauroyl diethoxy isethionate, and formulation 2 containing a combination of sodium lauroyl diethoxy isethionate and sodium cocoyl isethionate were significantly milder (p=0.03 for both formulations relative to comparative) relative to comparative composition containing only sodium cocoyl isethionate. These in vivo mildness results corroborate the indications of mildness suggested by the zein tests.

EXAMPLE 6

Lather Volumes

| | Composition 3 | Composition 4 | Comparative |
|---|---|---|---|
| Sodium cocoyl diethoxy isethionate | 49.8 | 33.4 | — |
| Sodium stearoyl diethoxy isethionate | — | 16.4 | — |
| Sodium cocoyl isethionate | — | — | 49.8 |
| Sodium tallowate/cocoate | 8.0 | 8.0 | 8.0 |
| Sodium stearate | 3.0 | 3.0 | 3.0 |
| Sodium alkylbenzene sulfonate | 2.0 | 2.0 | 2.0 |
| Fatty acid | 24.0 | 22.1 | 23.2 |
| Sodium chloride | 5.72 | 8.55 | 0.35 |
| Sodium 2-[2-(2-sulfoethoxy) ethanol | 1.7 | 1.4 | — |
| Sodium isethionate | — | — | 4.7 |
| Titanium dioxide | 1.0 | 1.0 | 1.0 |
| Water, fragrance, preservatives | to 100% | | |

Objective Lather Volumes

This test involved rotating the toilet bar 15 half turns under running 95° F. water. The bar was then set aside and the resulting lather was worked by hand for 10 seconds. A measuring funnel was then placed over the hands and both were lowered into a sink filled with water to the 0 ml mark on the measuring funnel. When the hands were fully immersed, they were removed from beneath the funnel. The funnel was then lowered to the bottom of the sink and lather volume was measured.

| Bar | Lather Volume (ml) |
|---|---|
| 3 | 94 |
| 4 | 97 |
| Comparative | 98 |

All bars tested had excellent lather volumes. Bars 3 and 4 containing diethoxy isethionates lathers as well as a commercially available comparative bar containing nonethoxylated isethionate.

EXAMPLE 7

Light Duty Liquid Containing Ethoxylated Isethionates

A composition containing the following ingredients may be prepared.

| Component | % By Weight |
| --- | --- |
| Ammonium alkyl benzene sulfonate | 19.0 |
| Sodium lauroyl/myristoyl diethoxy isethionate | 11.0 |
| Lauric/myristic monoethanolamide | 3.0 |
| Sodium xylene sulfonate | 5.0 |
| Preservative, fragrance, dye and water | to 100% |

EXAMPLE 8

Hand or Body Cleanser Containing Ethoxylated Isethionates

A composition containing the following ingredients was prepared.

| Component | % By Weight |
| --- | --- |
| Sodium lauroy/myristoyl diethoxy isethionate | 13.0 |
| Coco amido propyl betaine | 4.5 |
| Carbopol 940* | 1.0 |
| Laponite | 0.05 |
| Lauric/myristic acid | 5.6 |
| Sodium chloride | 2.8 |
| Preservative, fragrance and water | to 100% |

*About 1% cross-linked polyacrylic acid having a molecular weight of about 4 million

We claim:

1. A compound or mixture of compounds having the formula

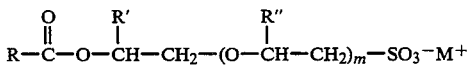

wherein R is a straight chain alkyl group having 8 to 18 carbons, m is an integer from 2 to 4, R' and R'' are hydrogen or an alkyl group having 1–4 carbons, and $M^+$ is a monovalent cation.

2. A compound according to claim 1, wherein R'' may differ from one group to another.

3. A compound according to claim 1, wherein the monovalent cation is selected from the group consisting of sodium, potassium and ammonium.

4. A compound according to claim 1, wherein R may vary within the mixture of compounds.

* * * * *